(12) United States Patent
Lacy

(10) Patent No.: US 6,483,114 B1
(45) Date of Patent: Nov. 19, 2002

(54) POSITRON CAMERA

(75) Inventor: Jeffrey L. Lacy, Houston, TX (US)

(73) Assignee: Proportional Technologies, Inc., Houston, TX (US)

(*) Notice: Subject to any disclaimer, the term of this patent is extended or adjusted under 35 U.S.C. 154(b) by 0 days.

(21) Appl. No.: 09/531,213

(22) Filed: Mar. 20, 2000

(51) Int. Cl.$^7$ .............................................. G01T 1/164
(52) U.S. Cl. ................................................. 250/363.03
(58) Field of Search ............................ 250/363.03, 374

(56) References Cited

U.S. PATENT DOCUMENTS

| | | | | |
|---|---|---|---|---|
| 2,596,080 A | * | 5/1952 | Raper et al. | .................. 313/93 |
| 3,207,938 A | * | 9/1965 | Anton | ..................... 250/374 X |
| 3,483,377 A | * | 12/1969 | Borkowski et al. | ......... 250/374 |
| 4,983,841 A | * | 1/1991 | Stewart et al. | ............ 250/358.1 |
| 5,071,381 A | * | 12/1991 | Schieber | ................. 250/374 X |

OTHER PUBLICATIONS

Avery, R.E., et al., Performance of 2mm radius straw tube drift cells, IEEE Transactions on Nuclear Science, vol. 40, No. 4 (Aug. 1993), pp. 578–582.*

Jeavons, A. P.; Chandler, R.A.; and Dettmar, C.A.R.; *3D HIDAC–PET Camera with Sub–millimetre Resolution for Imaging Small Animals*, IEEE Transactions on Nuclear Science, (Jun. 1999), vol. 46, No. 3, pp. 468–473.

Conti, M.; Del Guerra, A.; Habel, R.; Mulera, T.; Perez–Mendez, V.; and Schwartz, G.; *Use of a High Density Lead Glass Tubing Projection Chamber in Positron Emission Tomography and in High Energy Physics*, Nuclear Instruments and Methods in Physics Research A255 (1987), pp. 207–212.

Jeavons, A.; Hood, K. Herlin, G.; and Parkman, C; *The High Density Avalanche Chamber for Positron Emission Tomography*, IEEE Transactions on Nuclear Science, vol. Ns–30, No. 1, (Feb. 1983), pp. 640–645.

Jeavons, A.P. and Cate, C., *The Proportional Chamber Gamma Camera*, IEEE Transactions on Nuclear Science, vol. NS–23, No. 1, (Feb. 1976), pp. 640–644.

Jeavons, A.P.; Charpak, G.; and Stubbs, R.J., *High–Density Drift Spaces*, IEEE Transactions on Nuclear Science, vol. NS–22, (Feb. 1975), pp. 297–300.

* cited by examiner

Primary Examiner—Constantine Hannaher
Assistant Examiner—Shun Lee
(74) Attorney, Agent, or Firm—Akin, Gump, Strauss, Hauer & Feld, L.L.P.

(57) ABSTRACT

A structure for detection of radiation emitted by positron annihilation comprising a thin wall tube the inner surface of which is covered with an electrically conductive coating which is encompassed and enclosed by a spaced apart thin layer of lead, bismuth or an alloy thereof, an electrically conductive wire element coaxially positioned within said tube and an electrically insulative and pressure retaining element closing each tube end to contain there within from 0.1 to 10 bar of a gaseous atmosphere comprising argon together with a quench gas component or another suitable counting gas; and a PET imaging camera having closely packed arrays of a plurality of such tube structures.

11 Claims, 6 Drawing Sheets

Figure 2. (a) Longitudinal tube packing configuration with tubes orthogonal to incident radiation
(b) Radial tube packing configuration with tubes parallel to incident radiation Figure 4. Single straw tube element used in pilot testing, 5 mm diameter body, 10 cm length, 0.0015" Mylar™ thickness, 20 μm anode wire operated with flow through argon/ethane (50/50).

POSITRON CAMERA

CROSS-REFERENCE TO RELATED APPLICATIONS

Not applicable.

STATEMENT REGARDING FEDERALLY SPONSORED RESEARCH

Not applicable.

BACKGROUND OF THE INVENTION

1. Field of the Invention

This invention relates to detector device that may be used to detect radiation emitted by positron annihilations.

2. Description of the Related Art

Positron emission tomography (PET) is a powerful imaging technique providing capabilities which no other technology is likely to match. Its most unique feature is its ability to image tissue differentiated by function. In particular, the field is currently dominated by use of the imaging agent 18-FDG, which is a glucose analog. This agent is capable of labeling tissue in proportion to the tissue's ability to metabolize glucose. Such imaging shows great promise in the field of oncology since many tumors have altered metabolic processes relative to surrounding normal tissue. As a result, a large variety of primary and metastatic tumors are well visualized with the technique. No other technique is capable of distinguishing tissue according to its metabolic status.

Furthermore, PET produces three-dimensional imaging with unparalleled quantitative content. The basic high quality imaging characteristics of PET, including high sensitivity, attenuation correction, high contrast, and fully quantitative 3-dimensional character, enhance the potential of this technology even further. Finally, the chemistry of PET radiopharmaceuticals is currently in its infancy. It is very likely that, with wide availability of the imaging devices, even more powerful radiopharmaceuticals will follow.

Some of the promising applications of the 18-FDG radiotracer (half life=110 minutes) include imaging of brain tumors (DiChiro G. Positron emission tomography using [18-F]fluorodeoxyglucose in brain tumors: a powerful diagnostic and prognostic tool. Invest Radiol 1986; 22: 360–371; Coleman R E, Hoffinan H M, Hanson M W, Sostman H D, Schold S C. Clinical application of PET for the evaluation of brain tumors. J. Nucl. Med. 1991; 32:616–622), lung cancer (Patz E F, Lowe V, Hoffinan J M, et al. Evaluation of focal pulmonary abnormalities with [18-F]-fluoro-1-deoxyglucose and positron emission tomography. Radiology 1993; 188: 487–490.; Gambhir S S, Hoh C K, Phelps M E, Madar I, Maddahi J. Decision tree sensitivity analysis for cost-effectiveness of FDG-PET in the staging and management of non-small-cell lung carcinoma. J Nucl Med 1996; 37: 1428–1436; Patz E F, Lowe V J, Hoffinan J M, Paine S S, Harris L K, Goodman P C. Persistent or recurrent brochogenic carcinoma: detection with PET and 2-[18-F]-2-deoxy-D, glucosee. Radiology 1994; 191: 379–382), melanoma, lymphoma, colorectal carcinoma, breast cancer, head and neck cancer, gynecologic malignancy and bone and soft tissue malignancy (Conti P S, Lilien D L, Hawley K, Kepper J, Grafton S T, Bading J R. PET and [18-F]-FDG in oncology: a clinical update. Nucl Med Biol 1996;23: 717–735). Regional distribution centers are actively being established in preparation for broad usage of the 18-FDG radiopharmaceutical.

Unfortunately, PET camera technology is poorly suited for many important oncology applications, in which large regions of the body frequently need to be imaged. The typical ring style PET cameras offer a limited 12–16 cm axial field of view. Therefore, for imaging of large longitudinal sections of the body, acquisition of many individual slice images with sequential translation of the patient along the axis of the camera is required. These procedures can and frequently do require several hours of imaging, when large areas of the body are scanned for metastatic disease, for example. Clearly, such multiple view imaging also reduces sensitivity within any given imaging slice due to the limited time available for each region. The limited field of view of current PET detectors is dictated primarily by the high cost of the large array of crystals and photomultiplier tubes (PMT). In PET imaging, positron annihilation photons at 511 keV are imaged in coincidence, classically with large arrays of crystal detectors. These detectors must encompass a large portion of the 360 degree geometry around the patient. They must also be capable of stopping the 511 keV gammas with high efficiency. Furthermore, excellent time resolution is required because of the high singles rate and the large number of crystals needed. Because of this combination of requirements, classical PET cameras utilize crystals of BGO ($Bi_4Ge_3O_{12}$) (Moses W W, Derenzo S E, Budinger T F. PET detector modules based on novel detector technologies. Nucl Instr Meth 1994; A 353: 189–194). The high Z (mass number) of the material (principally bismuth) is advantageous for scatter-free detection of 511 keV by the photoelectric process. In NaI, over 75% of the interactions are compton scatter, which frequently results in multiple interaction points in the crystal array. If such scattered events are counted, many erroneous events result, and scatter is included. If they are not counted, than the upper limit on efficiency is less than 25%. By contrast, BGO provides a 43% photoelectron interaction fraction, yielding much cleaner and more efficient imaging. Crystal detectors of BGO are expensive and produce limited light output, driving up the cost of photomultiplier tubes. The base materials cost of assembled crystals and photomultipliers runs between $350,000 and $700,000 in today's cameras, and as a result the largest longitudinal field of view available commercially is limited to 24 cm (Moses W W, Derenzo S E, Budinger T F. PET detector modules based on novel detector technologies. Nucl Instr Meth 1994; A 353: 189–194).

Because of this high fixed materials cost, totally assembled and supported cameras cost from $1.5 million to over $3 million. Largely because of these exceedingly high costs, only about 60 dedicated PET imaging centers are in operation in the U.S. The small number of facilities combined with the limitation of large field of view imaging means that a very small fraction of the diagnostic imaging need for oncology patients is being met with today's technology.

In the hope of reducing high instrument cost and in order to increase the field of view, alternative systems are being actively pursued in the industry. Moses et al. have recently summarized the technical characteristics desired for high quality PET detectors (Moses W W, Derenzo S E, Budinger T F. PET detector modules based on novel detector technologies. Nucl Instr Meth 1994; A 353: 189–194). These requirements, listed in order of decreasing importance, are: high efficiency (>85%), high spatial resolution (<5 mm FWHM), low cost (<$600/sq. inch), low dead time (<4 $\mu$sec/sq. inch), good timing resolution (<5 nsec FWHM), and energy resolution (<100 keV FWHM). The problem of identifying a lower cost PET detector has been exceptionally intractable. The largest effort has focused on application of large area single crystal NaI devices in paired geometry. Such dual imaging systems are widely available for emission tomography, and the hope in the nuclear medicine instrumentation industry is that such cameras could provide a lower cost alternative for at least limited work with 18-FDG. However, these systems have very severe drawbacks caused by the gender and geometry of their crystals. Although the 1 cm thick NaI crystal utilized by most of these systems is adequate for Tc-99m, it provides only a 5% photoelectron efficiency at 511 keV, driving the coincidence efficiency down to an extremely limiting 0.2%. This efficiency is more than two orders of magnitude less than that of the conventional BGO PET camera. As a result, such systems require extremely lengthy data acquisition times. Furthermore, because very high singles rates are present in the uncollimated geometry, these systems saturate at very low injected activity levels.

Another alternative that has been explored is the use of the multiwire proportional chamber (MWPC). It is widely recognized that multiwire systems employed together with 511 keV converter modules can provide PET images at substantially lower costs. Despite extensive development efforts, however, these systems have very limited detection efficiencies of 10–30%, and depending on the converter system utilized, have either poor coincidence time resolution of 88 nsec compared to 5 nsec for the BGO systems, or poor spatial resolution of 5–11 mm compared to less than 6 mm for the BGO systems (Wells K, Visvikis D, Ott R J. Performance of a $BaF_2$-TMAE detector for use in PET. IEEE Trans Nucl Sci 1994; to be published; McKee B T A, Dickson A W, Howse D C. IEEE Trans Med Img. MI-13 (1994) 176).

SUMMARY OF THE INVENTION

A novel wire detector design is here proposed which in part is based on the modern straw tube technology being extensively employed in contemporary high energy physics. Such straw tube detectors can be very inexpensively produced to cover large volumes in close-packed arrays of 5 mm or smaller individual tube diameter. Because of the small size and use of modern, high-speed counting gases, these tubes can achieve very good time resolution of 10–25 nsec (FWHM). Given the very thin walls (0.001"–0.0015") of such tubes, it is proposed to wrap them with thin lead converters or to incorporate such thin lead foil in the wall itself which can effectively convert the 511 keV radiation to energetic photoelectrons with sufficient energy to easily penetrate the tube wall. Such lead converter equipped tubes may be employed in an annular, close-packed array, with a sufficient number of tubes and therefore aggregate lead foil thickness to effectively stop 511 keV radiation. Readout of the converter wrapped tube struck by an event together with longitudinal position along the converter wrapped tube will allow position determination in three dimensional space of 5 mm FWHM or better. Such readout techniques have been well developed and proven in the high energy physics field. The estimated cost of such a detector array, based on documented costs of existing high energy physics systems scaled up to volume commercial production, is $25 per square inch of detector surface, or about 20 times less than the $600 per square inch for the BGO crystal array (Moses, 1994). Through reduction of the lead foil thickness to a minimum providing efficient photoelectron escape into the thin-walled straw tube, high detection efficiency approaching that of BGO is feasible. Therefore, this design can provide a PET imaging system with excellent characteristics and with substantial reduction of cost. It would thereby be feasible to construct economical PET systems of far larger area, potentially encompassing the entire patient torso, which would be of great benefit for oncology applications utilizing 18-FDG.

DESCRIPTION OF PREFERRED EMBODIMENTS

Here it is proposed to use thin Pb converters, which can provide essentially any required degree of reduction of Pb converter thickness, in order to obtain efficient photoelectron escape, while at the same time acceptable time resolution. This is accomplished through use of straw detectors which have become a very well developed inexpensive technology in high energy physics. The radiation detectors of this invention comprise a thin plastic tube, typically 4–5 mm in diameter, coated on the inner wall with a vapor deposited conductive coating, such as copper or aluminum. The plastic wall thickness is 0.002"–0.0005", and the conductive metal layer is of negligible 1,000 angstrom thickness. The basic plastic tube complete with conductive metal coating can be manufactured in mass quantities by utilizing techniques developed in the soda straw industry and since no expensive, consumable materials are required, the cost of such tubing is very small. A central anode wire of diameter 20 microns is coaxially tensioned in the center of the tube. These tubes are routinely produced in lengths of 1 m or longer and are operated for months in large arrays, numbering tens of thousands, in high energy physics experiments.

Figure 1:
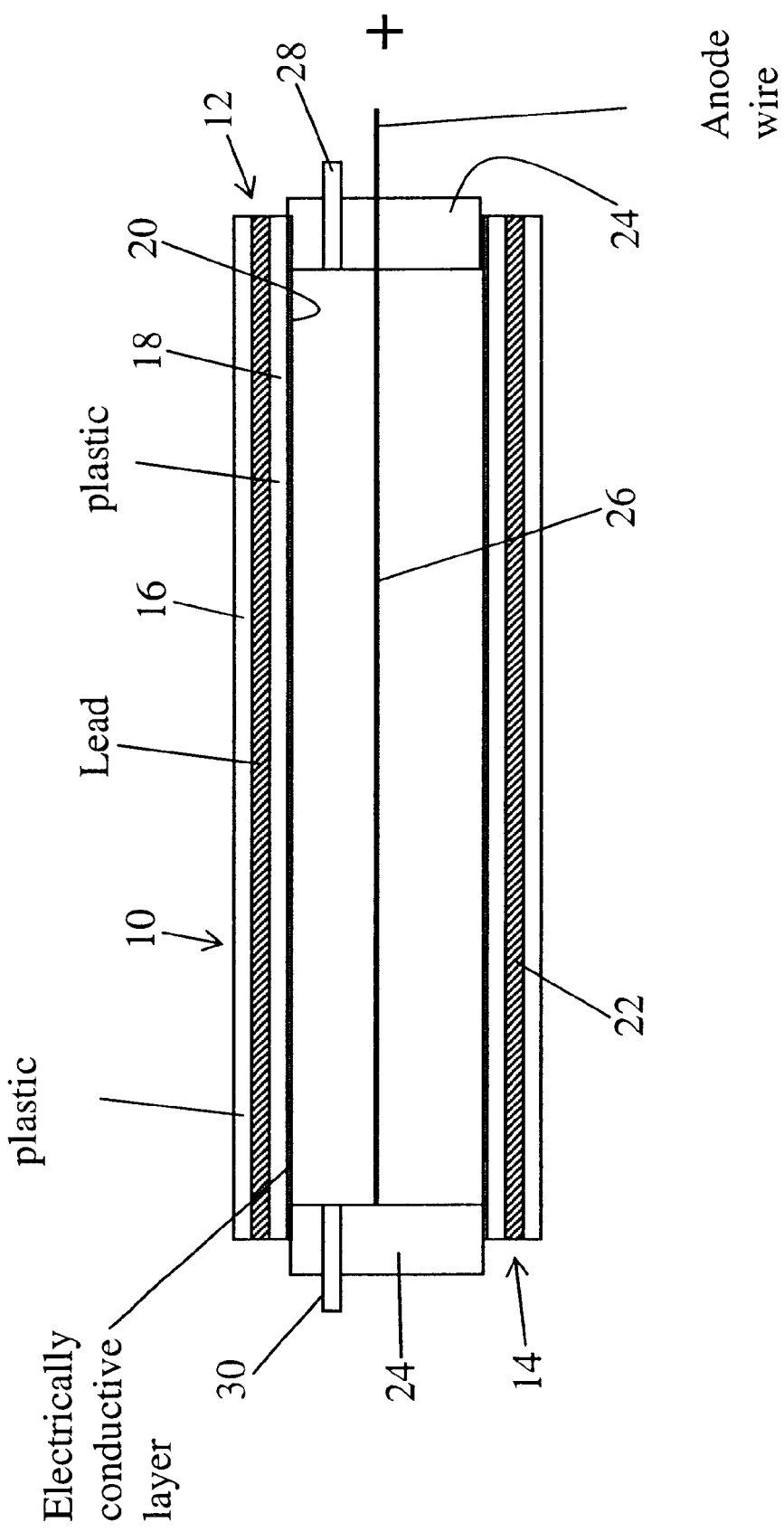
FIG. 1 schematically illustrates the structure of a lead converter equipped detector tube constructed in accordance with this invention.

These tubes in close-packed arrays are employed along with the thin lead foil converters wrapped around each straw or incorporated into the wall during fabrication to efficiently detect the 511 keV gammas. A radiation detector tube is depicted in side-section view in FIG. 1. The radiation detector tube comprises a thin wall tube 10 having a proximal 12 and distal 14 end and an outer 16 plastic surface and inner 18 plastic surface, said inner plastic surface 18 is covered with an electrically conductive coating 20 exterior to which and out of electrical contact with which there exists a thin layer comprising lead or bismuth or an alloy thereof 22 which encloses this electrically conductive coating. This thin layer comprising lead or bismuth or an alloy thereof 22 may be located about the outer surface of the thin wall tube or may be integrated within the wall structure of the tube itself as shown. The detector tube 10 also comprises a pressure retaining and electrically insulative closure means 24 by which each of the proximal and distal tube ends are closed. One closure means 24 is provided with a small gas input port 28 and the other closure means 24 is provided with a small gas output port 30. Further, the radiation detector tube contains an electrically conductive wire element 26 coaxially positioned within said tube and electrically insulated from the conductive coating of the inner surface thereof. The radiation detector tube contains a gaseous atmosphere at a pressure of 0.1 to 10 barr and this gaseous atmosphere comprises argon or $CF_4$ together with another gas component including argon, ethane, $CF_4$ or other suitable proportional counting gas.

Figure 2:
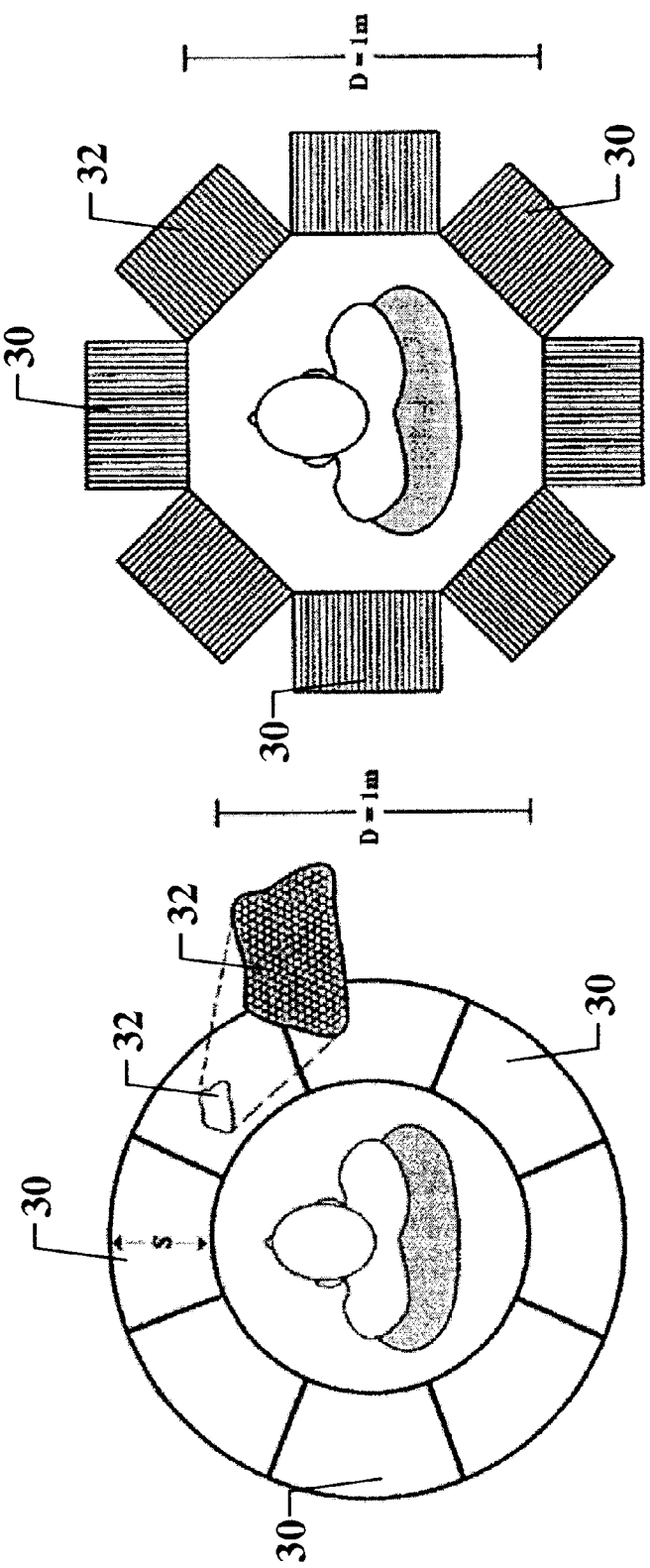
FIG. 2, view A schematically illustrates a PET imaging camera in proximity to a patient from a top-down cross-sectional patient perspective wherein arrays of converter equipped detector tubes of this invention are in a longitudinal tube packing configuration with the converter equipped detector tubes orthogonal to incident radiation; and view B illustrates a PET imaging camera in relation to a patient to be imaged wherein the array of converter equipped detector tubes are in a radial tube packing configuration with the detector tubes parallel to incident radiation.
Figure 3:
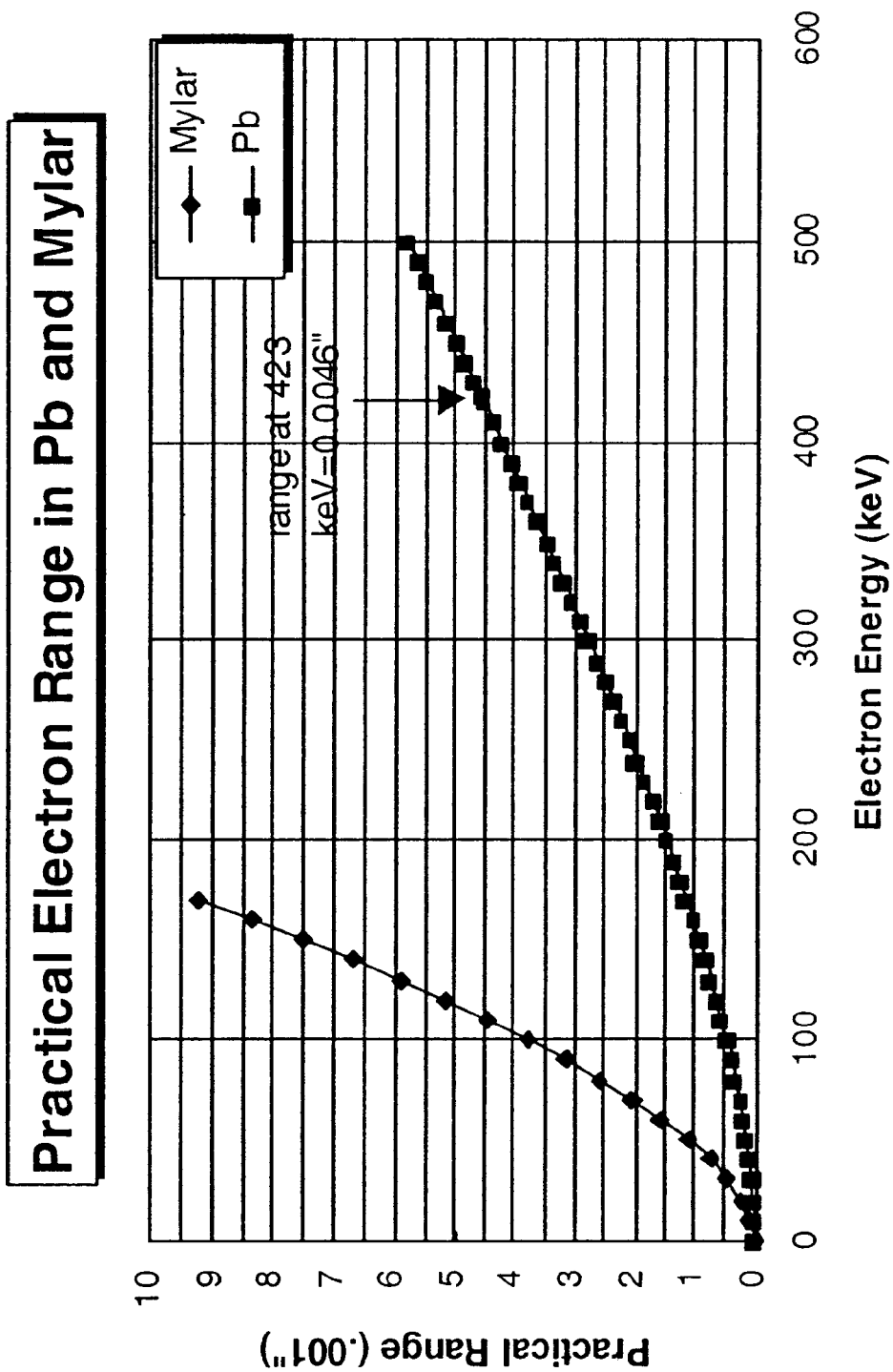
FIG. 3 graphically illustrates the practical electron range for different electron energies in each of a lead material and a mylar plastic.

Two possible packing configurations of these tubes are depicted in FIG. 2, (a) and (b). FIG. 2(a) illustrates a longitudinal tube packing configuration wherein arrays 30 of multiple tube detectors 32 are orthogonal to incident radiation emerging from a patient. FIG. 2(b) illustrates a radial tube packing configuration wherein the detector tubes of an array 30 are parallel to incident radiation. In either configuration, the total lead content of the converter structure is desirably set to at least about 1 photoelectric attenuation length of lead, or 1.1 cm. An expression for the number of tubes required to achieve such thickness is given as follows. In a 3-dimensional structure of tubes packed orthogonally, i.e. with axes lying on lines with a spacing of D=outside tube diameter, the equivalent Pb thickness encountered from traversing a 1 cm depth through a collection of tubes is: t/D, where t=Pb wall thickness and D=outside tube diameter of a tube. Therefore, in order to provide one photoelectric attenuation length, the radial thickness (S) of the detector array, shown in FIG. 2(a), equals 0.35 D/t cm. An estimate of the optimal lead foil thickness for the converter can be obtained by examining the practical electron range curve in lead, depicted in FIG. 3. A 423 keV photoelectron is stopped 90% of the time in a Pb depth of just over 0.004". Thus, most photoelectrons liberated in a foil of thickness 0.002" would escape and emerge from one or the other wall with enough energy to penetrate the 0.001" wall of the straw. Because of the low density of plastic, only 60 keV energy is needed to penetrate plastic (such as MYCAR) tube of 0.0015" wall thickness (see FIG. 3). Once in the tube, this heavily ionizing electron will be detected with very high efficiency. If every tube is equipped with a Pb converter, it must be considered that 50% of the photoelectrons emerging from a converter wrapping will emerge towards the outside of the tube and will therefore have to penetrate into a neighboring tube to be detected. In order to do this, they must traverse another full lead foil thickness. Therefore, conservatively one would use a 0.001" lead foil in every tube. Then, at most, regardless of the direction in which the electron were liberated, it would have to traverse no more than half of its practical range in lead in order to reach the interior of one of the tubes. If one then takes a commonly employed straw diameter of 0.4 cm and this foil thickness of 0.0025 cm, then from the above expression, S=0.35 D/t=56 cm. Then from the configuration of FIG. 2(a), one may compute the number of straws required by simply obtaining the area of the array annulus filled by the tubes. For a generous and commonly used patient space inner bore diameter of 100 cm, this number comes to 171,000 straws. Typical straws of this type operated at accelerator laboratories have a length of 1 m or more and can be read out longitudinally with an accuracy of at least 1% of the length of the tube with simple charge division or resistive wire techniques. It is therefore practical to have a 50 cm longitudinal dimension and achieve a PET slice resolution of 5 mm or better. Based on use in high energy physics, cost of straw materials with such characteristics is estimated at no more than $1 per straw. Therefore, a generous, whole patient torso PET camera with 50 cm axial field of view could be constructed at a materials cost under $200,000. A similar BGO system would cost at least $1.5 million dollars in crystals and PMTs. Thus, the straw/lead converter system can reduce costs by approximately an order of magnitude and thereby make it economically feasible to achieve whole body PET imaging. Unlike other systems offering larger fields of view, this technique can provide high quality characteristics in all areas.

Addressing the list of specifications detailed by Moses et al., PET detector modules based on novel detector technologies; Nucl. Instr. Meth. 1994; A 353: 189–194, the system stacks up as follows. Sensitivity: Although it is unrealistic to expect 100% converter efficiency since some photoelectrons simply will not emerge from the foil converters, this efficiency can be far higher than any system other than BGO and may approach the 85% figure of BGO. The photoelectron fraction of pure lead offers a significant advantage over BGO, 55% vs. 43%. Spatial Resolution: Assuming that the converter foil thickness is optimized so that two-straw activation is infrequent as anticipated, the system should have a spacial resolution, FWHM, at or better than the tube diameter, which can comfortably be 4 mm or even smaller. Cost: An order of magnitude reduction should be possible. Dead Time: Straw tube signals have a rise time of 10 nsec and a duration of about 30 nsec. Therefore, dead time is 5–10 times less than BGO. Time Resolution: The maximum time uncertainty for a 4 mm tube and ethane, $CF_4$ filling is 20 nsec, which is the gas drift time from the tube periphery to the anode wire. This gives a FWHM time jitter of about 10–15 nsec. Such time resolution is routine in high energy physics work. Energy Resolution: Although not readily apparent, intrinsic energy resolving characteristics are built into the foil converter technique, due to the rapid decrease of photoelectron range with energy. It is much less probable that a Compton scattered gamma of 200–300 keV will produce a photoelectron capable of emerging from the converter. The fact that pure lead forms the detection medium greatly reduces the need for energy resolution since there is much less scatter in the detector compared with BGO and other systems.

A positron camera constructed in accordance with this invention has the potential to greatly enhance the practical application of PET in very important clinical areas of oncology, where its highly unique capabilities to differentiate tissue based on metabolism can provide their true clinical benefit. With a large area, high sensitivity camera, it is very likely that the sensitivity for small tumor identification will be greatly increased, with substantial benefits in early and accurate diagnosis of metastatic disease and thus with clear, highly significant benefits to cancer patients. Also, availability of such detector technology will likely spur further development of PET radiopharmaceuticals with far-reaching effects. As a side benefit, this straw tube Pb converter technology can be employed in smaller scale systems dedicated to brain and/or heart imaging, also with substantial cost reduction. Although cardiac PET is widely recognized as superior to single photon emission tomography (SPECT), because of its high cost, its utilization in myocardial perfusion imaging is negligible in scope in comparison to SPECT. The same case prevails for brain imaging despite the even more compelling advantages of PET. Both of these situations are readily remedied by the 10-fold reduction in instrumentation cost afforded by this invention.

In order to demonstrate the concept of lead foil conversion/straw tube detection, some limited pilot studies were performed with straws prepared for the purpose. The straw tube unit has a 10 cm long active length, is 0.5 cm in diameter, and uses a 20 micron gold-plated tungsten anode wire. The wall thickness of the shell of the straw is 0.0015" plastic (such as MYLAR) with a 1,000 angstrom vapor-deposited copper coating on the interior surface. In this short length, it is possible to operate the tube free-standing since, despite the thin walls, the tube supports the 20–30 gram tension of the anode wire and maintains an accurate cylindrical geometry. A generic low-cost gas mixture of 50% argon, 50% ethane was utilized and flowed slowly through the tube. Straw signals were amplified using a fast current amplifier having a rise time of 25–30 nsec. These signals were fed to a LeCroy model 821 linear threshold discriminator to obtain a fast timing pulse. Thin lead foil of thickness 0.00093" was carefully wrapped around the tube and served as the gamma converter.

The operation of the tube was plateaued by using the following procedure. The lower discriminator threshold was set just above the amplifier noise so that no events were recorded with high voltage (HV) off. The tube was irradiated with a small 511 keV source, HV was increased in successive 100 volt steps, and the discriminator count rate was observed. At a high voltage of 1600 volts, the discriminator rate reached an asymptotic maximum. Increase to 1700 volts produced less than 1% change in rate. The tube produced occasional discharge at 1900 volts. Therefore, plateaued operation was attained at 1600 volts, at which the tube was then operated. The tube provided highly stable operation at this voltage over the two week period during which pilot studies were performed.

Figure 4:
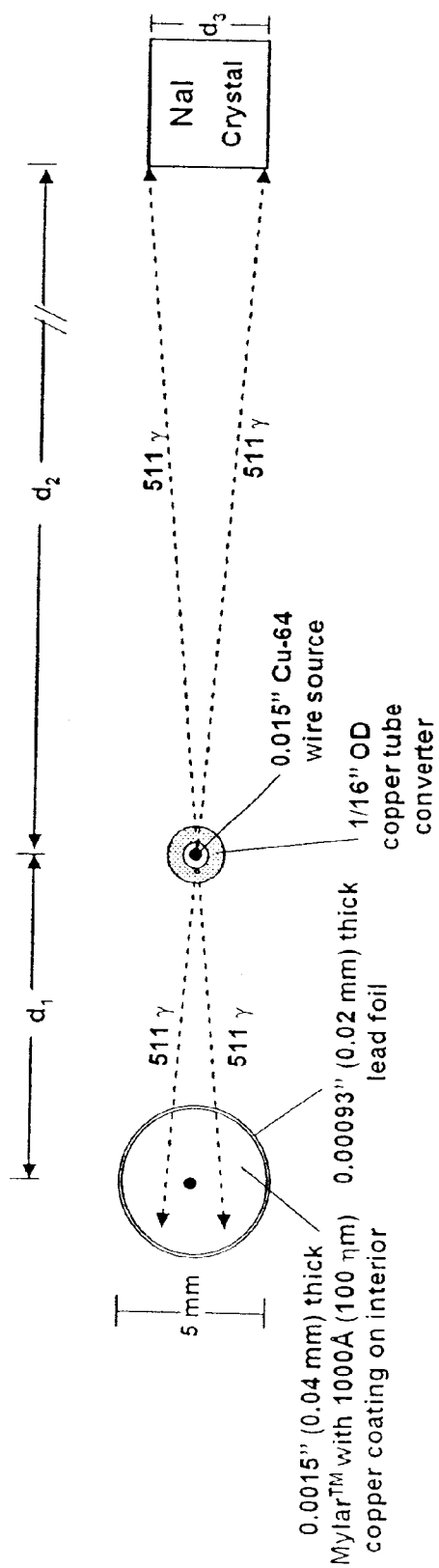
FIG. 4 schematically illustrates a lead converter equipped tube, source and crystal geometry used to measure straw/converter efficiency at 511 keV.

In order to demonstrate the concept of Pb-foil conversion, the tube was configured as shown in FIG. 4. A small line positron source, equipped with an absorber to convert the positrons near the point of origin, was positioned approximately 1 cm (=$d_1$) from the straw's central axis. The Cu-64 line positron source was prepared as follows. A 0.015" Cu wire was irradiated with 7.5 MeV deuterons to produce 10–100 $\mu$Ci of Cu-64. The purity of the Cu-64 produced was assessed by HPGe spectroscopy and was found to be 99% or greater. The small wire was slipped into a 1/32" brass tube which was in turn slipped into a 1/16" OD copper tube in order to provide ample material surrounding the wire to stop both the Cu-64 $\beta^-$ and $\beta^+$ emissions. Since the endpoint energies of these electrons are 578 keV and 653 keV, respectively, the copper and brass tubing provided ample stopping power. A 1" NaI crystal was positioned on the other side of the source at a distance of 10–20 cm (=$d_2$). The NaI crystal was used for photopeak detection of 511 keV positron conversion gammas. The geometry was chosen so the 511 keV gamma opposing the NaI detected gamma was assured of traversing the straw and its Pb-converter near the center of the tube (~middle third) in the vertical dimension. Therefore, every event chosen by NaI should have a clean 511 keV gamma passing through the sensitive geometry of the straw, and the sensitivity of this single element is obtained by recording the ratio of the NaI counts to the NaI/straw coincidence counts. Lengthy, high statistics measurements were obtained to determine the sensitivity. The photoelectric attenuation coefficient of Pb at 511 keV is 0.079 cm$^2$/g, and for a lead thickness of 0.00093" is 0.0268 g/cm$^2$. The fraction of 511 conversions interacting by photoelectric effect therefore in this lead foil is F=(0.0268 g/cm$^2$)×(0.079 cm$^2$/g)=0.0021 or 0.21%. On the other hand, since the Compton scatter cross-section is 0.045 cm$^2$/g, the fraction of the beam suffering Compton scatter is 0.12%. These percentages are also what one would expect to detect in a tube wrapped with 0.00093" lead, if the photo- or Compton electrons all escape from the lead foil, since the beam is traversing both front and back walls of the tube, doubling the target thickness, but only 50% of the electrons are expected to emerge from the inside of the converter and trigger the tube. The other 50% escape from the other surface and will rarely be detected with this single tube. Measurement of coincidence fraction for these conditions gave 0.26%±0.006%. This value is consistent with the expected detection of the majority of photoelectrons and some much smaller fraction of the Compton electrons, which escape from the foil less effectively due to their degraded energy. This measurement is consistent with a foil of 0.001" thickness, producing a high sensitivity for the overall camera, given enough tube elements to stop the 511 gamma efficiently, as per previous estimates for this foil thickness. Of course, it is essential that measurements also be performed to establish what happens to the electrons emitted from the outside of the converter tube wall. Most of them should easily penetrate the 0.001" Pb-foil of neighboring tubes and produce straw signals as well. This measurement was outside of the scope of the pilot work.

Figure 5:
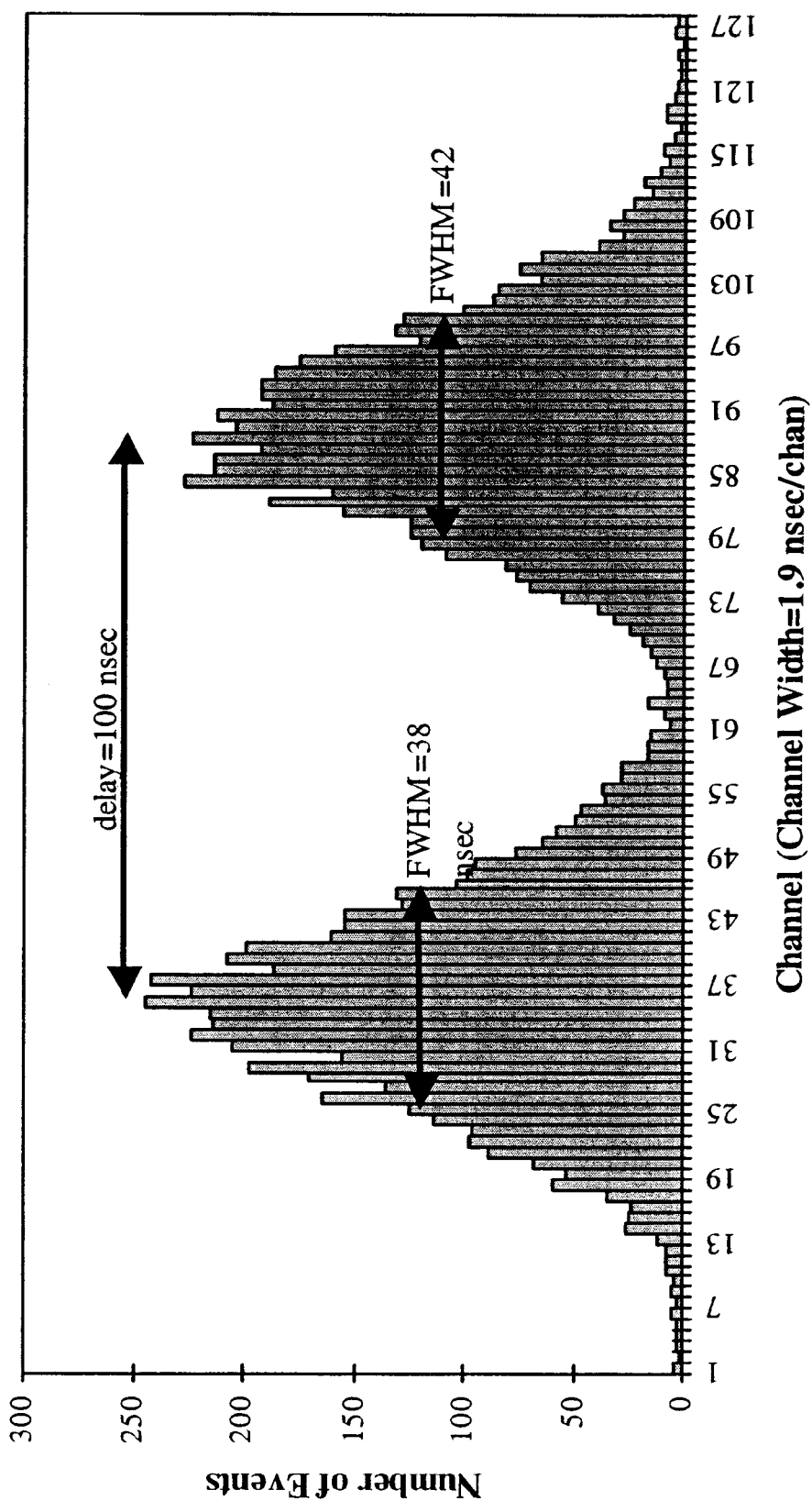
FIG. 5 graphically illustrates the timing resolution with (right) and without 100 nanosecond delay.
Figure 6:
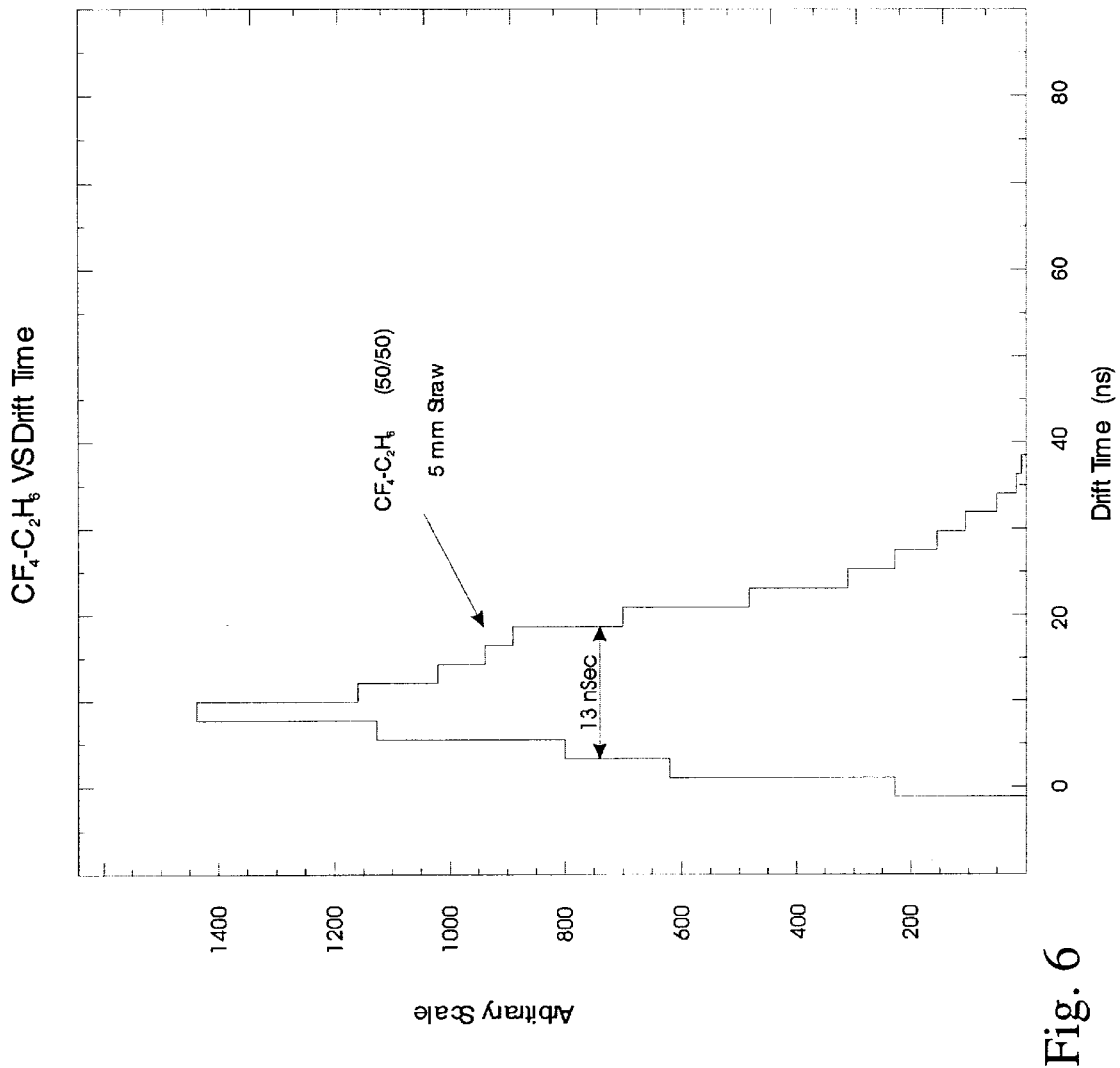
FIG. 6 shows the time resolution of a 5 mm tube filled with ethane/$CF_4$ (50/50).

Also, in this pilot study, the coincidence time resolution was examined between two of the straw tubes wrapped with 0.00093" Pb-converters positioned on either side of the Cu-64 wire source. The resulting time distribution is shown in FIG. 5. In order to obtain an accurate time calibration, two collections were performed successively, with and without a 100 nsec time delay added in the stop channel. Therefore, the peak separation provides a measure of the time scale, which is 1.9 nsec per channel. From the well-known drift speed of 5 cm/$\mu$sec in argon/ethane, the expected maximum tube to tube time difference can be no more than the length of time required to drift ionization from the straw periphery to the anode wire, which is 50 nsec. The measured peaks are somewhat wider than this. This effect is likely a consequence of the suboptimal preamplifier and simple threshold discriminator used in the test which degraded the signal timing substantially. FIG. 6 shows the time resolution of a 5 mm tube identical to the pilot unit but filled with ethane/CF$_4$ (50/50). The time resolution of this mixture is more than two times faster than argon/ethane, with a FWHM value of 13 nsec. Reduction of the tube diameter can improve this time resolution in proportion to the reduction. For example, for a reduction of the straw diameter to 4 mm, then the 13 nsec FWHM above would be reduced to 10.4 nsec FWHM.

The pilot study results are consistent with a highly functional PET imaging camera design as previously described using 0.001" thick lead foil converters. From the range-energy relationship, it would appear probable that this thickness for more optimum performance should be larger than 0.001", possibly 0.0015" or more. This is a very important determination as the number of tubes scales with the thickness of the foil utilized. In fact, this dependence is a higher power than linear since decrease of thickness of the detector stack, which is linear in foil thickness, allows removal of tubes from the periphery of the annular structure, where significantly more tubes are required per unit stack thickness. For example, if in the previously described tube count estimate but now using a 0.0015" foil for the estimate, the annulus thickness S would be reduced from 56 cm to 37 cm, and the tube count would decrease from 171,000 to 99,000.

Work regarding performance of various gas mixtures for high speed counting in high energy physics is quite extensive. It is well known that mixtures high in $CF_4$ have greatly enhanced drift velocities. For example, pure $CF_4$ can produce very high drift velocities, but is known to be somewhat unstable. Accordingly a small amount of other quench gases, such as ethane, may preserve the high drift velocity while stabilizing the performance. In most drift chamber applications, saturated drift is essential since a linear relationship between distance and time is needed and the drift field varies substantially in a proportional detector. In case of this new detector design, linearity is not required, and sacrifice of this characteristic may result in greatly reduced coincidence time window.

Methods of measurement of longitudinal tube position may be investigated in order to determine the optimal method for the PET Application. Many techniques for achieving this encoding have been reported in the high energy physics literature. Most of these have concentrated on very high resolution encoding aimed at submillimeter localization. In the case at hand, 3–4 mm FWHM resolution is the maximum required, but because of the very large number of tubes involved, it is very important to minimize complexity of both amplifiers and encoding techniques. The simplest approach is the charge (or current) division method, in which the signal amplitudes obtained at opposite ends of the anode wire are compared. Measurement on the order of 1% or better of the total wire length is easily achievable by this method.

An electronic readout system for a camera could be one wherein the conducting wire element of each tube is connected to a positive high voltage potential of about 1500 volts and in turn connected to a sensitive amplifier and timing discriminator providing threshold detection of signals produced on the wire and determination of the time of occurrence of such signals. The amplifier/discriminator circuitry is attached to both ends of each tube element and the coordinate of the interaction point along the longitudinal axis of each tube is determined by comparing signals either by time of arrival or amplitude. For a camera consisting of an array of tubes the electronic read-out system may be equipped with coincidence circuitry capable of identifying pairs of tubes being struck in coincidence by 511 kV positron conversion gamma rays with a time resolution of about 10 nanoseconds.

Alternatives to simple wrapping with lead foil may be explored with the goal of achieving economical and convenient means of assembly while preserving effective conversion of photoelectrons. One attractive approach is use of PbO powder with a binder to form a paint which could be applied to the straw's outer surface. Such a binder should add a negligible amount of low Z material to PbO, which itself is only 8% oxygen by weight. While it is important to preserve the high photoelectric interaction fraction of pure lead as much as possible, some degradation may be justified if assembly is markedly simplified. With an appropriate coating, it should be possible to produce a much longer, self-supporting tube, which could provide advantages in assembly and mounting. Another attractive approach is to incorporate lead, or possibly lead-bismuth alloy foil, into the straw assembly process. The straws are manufactured by winding narrow strips of plastic (such as MYLAR) on a cylindrical mandrel. If the metal foil is bonded to the outer surface of the copper-clad plastic (such as MYLAR) prior to this winding process, winding of the straw with lead converter in place within the straw wall can be accomplished. A much more rigid structure is produced in the process. Also the thin lead can be added as one of the strip elements during winding in such a way that a one layer lead foil is bonded within the wall.

The foregoing disclosure and description of the invention are illustrative and explanatory thereof, and various changes in the details of the illustrated apparatus and construction and method of operation may be made without departing from the spirit of the invention.

what is claimed is:

1. A structure for detection of radiation emitted by positron annihilation, comprising:

a thin wall tube having a proximal and distal end and an outer and inner surface, said inner surface covered with an electrically conductive coating which is encompassed and enclosed by a thin layer comprising lead which is spaced apart from said electrically conductive coating, a pressure retaining and electrically insulative tube enclosure means closing each of the proximal and distal tube ends, an electrically conductive wire element coaxially positioned within said tube out of contact with the electrically conductive coating of the inner surface thereof, and said tube contains a gaseous atmosphere at a pressure of at least one bar comprising argon and another gas component.

2. The structure of claim 1, wherein said thin layer of lead has a thickness of from about 0.00025 inch to 0.002 inch.

3. The structure of claim 2, wherein said thin wall tube is comprised of plastic which sums to a plastic wall thickness of from 0.0005 to 0.002 inch.

4. The structure of claim 3, wherein said thin wall tube has a length of at least about 25 cm.

5. The structure of claim 4, wherein said thin wall tube has an outer diameter of 5 mm or less.

6. The structure of claim 5, wherein said electrically conductive coating comprises vapor deposited copper, aluminum or nickel of a thickness of about 1000 Å.

7. The structure of claim 5, wherein said electrically conductive coating comprises a layer of carbon composite of thickness 0.0001" to 0.001" thickness.

8. A PET imaging camera, comprising diametrically positionally opposed detector arrays, each of said detector arrays composed of a plurality of closely packed detector tubes which detect radiation emitted by positron annihilation, each of said detector tubes comprising:

a thin wall tube having a proximal and distal end and an outer and inner surface, said inner surface covered with an electrically conductive coating which is encompassed and enclosed by a thin layer comprising lead which is spaced apart from said electrically conductive coating, a pressure retaining and electrically insulative tube enclosure means closing each of the proximal and distal tube ends, an electrically conductive wire element coaxially positioned within said tube out of contact with the electrically conductive coating of the inner surface thereof, and said tube contains a gaseous atmosphere at a pressure of 0.1 to 10 bar comprising argon and another gas component.

9. The camera of claim 8, wherein the conductive wire element of each tube is connected to a positive high voltage potential of about 1500 volts and in turn connected to an amplifier and timing discriminator providing threshold detection of signals produced on the wire and determination of the time of occurrence of such signals.

10. The camera of claim 8, wherein amplifier and discriminator circuitry is attached to both ends of each tube element and the coordinate of the interaction point along the longitudinal axis of each tube is determined by comparing signals from each end either by time of arrival or amplitude.

11. The camera of claim 9, further comprising coincidence circuitry capable of identifying pairs of tubes being struck in coincidence by 511 KeV positron conversion gamma rays with a time resolution of about 5–30 nanoseconds.

* * * * *